Figures 1, 2:
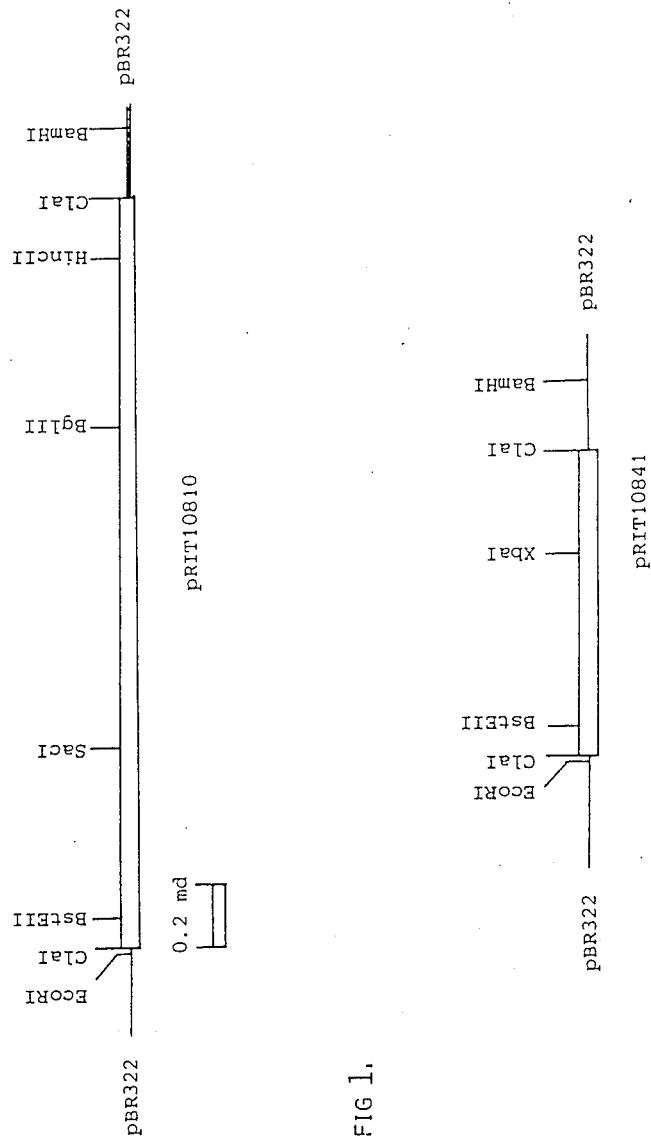

United States Patent [19]

Harford et al.

[11] Patent Number: 4,666,837

[45] Date of Patent: May 19, 1987

[54] DNA SEQUENCES, RECOMBINANT DNA MOLECULES AND PROCESSES FOR PRODUCING THE A AND B SUBUNITS OF CHOLERA TOXIN AND PREPARATIONS CONTAINING SO-OBTAINED SUBUNIT OR SUBUNITS

[75] Inventors: Nigel Harford, Overijse; Michel De Wilde, Rixensart, both of Belgium

[73] Assignee: SmithKline-RIT, Belgium

[21] Appl. No.: 381,083

[22] Filed: May 24, 1982

[51] Int. Cl.[4] ........................ C12P 21/00; C12P 21/02; C12P 19/34; C12P 21/04; C12N 15/00; C12N 1/00; C12N 1/20; C12R 1/19; C12R 1/63; C12Q 1/68; C12Q 1/04; C07H 21/04

[52] U.S. Cl. ........................................ 435/68; 435/70; 435/91; 435/172.3; 435/243; 435/253; 435/317; 435/849; 435/909; 435/6; 435/34; 435/71; 536/27; 935/11; 935/12; 935/29; 935/72; 935/73

[58] Field of Search ...................... 536/27; 435/68, 70, 435/91, 172, 253, 317, 849, 909, 172.3, 6, 34, 71, 243; 436/63, 94; 935/11, 29, 72–75

[56] References Cited

U.S. PATENT DOCUMENTS

| | | | |
|---|---|---|---|
| 4,293,652 | 10/1981 | Cohen | 435/91 |
| 4,328,209 | 5/1982 | Finkelstein et al. | 424/92 |
| 4,332,892 | 6/1982 | Ptashne et al. | 435/172 |
| 4,338,397 | 7/1982 | Gilbert et al. | 435/70 |
| 4,366,246 | 12/1982 | Riggs | 435/172 |

OTHER PUBLICATIONS

Covarrubias et al., "Construction and Characterization of New Cloning Vehicles V. Mobilization and Coding Properties of pBR322 and Several Deletion Derivatives Including pBR327 and pBR328", Gene 13: 25 (1981).

Biochemical Catalogue—Boehringer Mannheim, 1983, pp. 92–93.

Leder et al., "The Cloning of Mouse Globin and Surrounding Gene Sequences in Bacteriophage Lambda", Cold Spring Harbor Symp. Quant. Biol. 42: 299 (1978).

Houghton et al.: Nucleic Acids Res. 8, 2885 (1980).

Grantham et al.: Nucleic Acids Res. 8, 1893 (1980).

Roberts: Methods in Enzymology, vol. 68, pp. 27–41 (1979).

Pearson et al., Proc. Natl. Acad. Sci. U.S.A. 79:2976–2980 (1982).

Kaper et al., Abstr. Ann. Mtg. Am. Soc. for Microbiol. Abstr. No. B111, p. 36 (1982).

Kaper et al., Lancet 2 (8256):1162–1163 (1981).

Gennaro et al., Lancet 1239–1240 (May 29, 1982).

Duffy et al., J. Biol Chem 256 (23):12252–12256 (1981).

Spicer et al., Proc. Natl. Acad. Sci. USA 78(1) 50–54 (1981).

Dallas et al., Nature 288:499–501 (1980).

Yamamoto et al., J. Bacteriol 145 (2):850–860 (1981).

Kaper et al., Infect. Immun. 32(2):661–667 (1981).

Lai, J. Biol. Chem 252(20):7249–7256 (1977).

Mekalanos et al., Proc. Natl. Acad. Sci. USA 79:151–155 (1982).

Moseley et al., J. Bacteriol. 144 (1):444–446 (1980).

Holmgren Nature 292:413–417 (1981).

*Primary Examiner*—James Martinell

*Attorney, Agent, or Firm*—Edward T. Lentz; Janice E. Williams; Alan D. Lourie

[57] ABSTRACT

DNA sequences and recombinant DNA molecules comprising at least a portion coding for all or part of subunits A and/or B of cholera toxin are prepared by enzymatic digestion of DNA of *V. cholerae* strains, isolating specific fragments and inserting them in appropriate vectors and subunits A and/or B of cholera toxin are prepared by culture of microorganisms containing said modified vectors.

26 Claims, 6 Drawing Figures

```
          10         20         30         40         50
     ATGGTAAAGA TAATATTTGT GTTTTTTATT TTCTTATCAT CATTTTCATA
          60         70         80         90        100
     TGCAAATGAT GATAAGTTAT ATCGGGCAGA TTCTAGACCT CCTGATGAAA
         110        120        130        140        150
     TAAAGCAGTC AGGTGGTCTT ATGCCAAGAG GACAGAGTGA GTACTTTGAC
         160        170        180        190        200
     CGAGGTACTC AAATGAATAT CAACCTTTAT GATCATGCAA GAGGAACTCA
         210        220        230        240        250
     GACGGGATTT GTTAGGCACG ATGATGGATA TGTTTCCACC TCAATTAGTT
         260        270        280        290        300
     TGAGAAGTGC CCACTTAGTG GGTCAAACTA TATTGTCTGG TCATTCTACT
         310        320        330        340        350
     TATTATATAT ATGTTATAGC CACTGCACCC AACATGTTTA ACGTTAATGA
         360        370        380        390        400
     TGTATTAGGG GCATACAGTC CTCATCCAGA TGAACAAGAA GTTTCTGCTT
         410        420        430        440        450
     TAGGTGGGAT TCCATACTCC CAAATATATG GATGGTATCG AGTTCATTTT
         460        470        480        490        500
     GGGGTGCTTG ATGAACAATT ACATCGTAAT AGGGGCTACA GAGATAGATA
         510        520        530        540        550
     TTACAGTAAC TTAGATATTG CTCCAGCAGC AGATGGTTAT GGATTGGCAG
         560        570        580        590        600
     GTTTCCCTCC GGAGCATAGA GCTTGGAGGG AAGAGCCGTG GATTCATCAT
         610        620        630        640        650
     GCACCGCCGG GTTGTGGGAA TGCTCCAAGA TCATCGATGA GTAATACTTG
         660        670        680        690        700
     CGATGAAAAA ACCCAAAGTC TAGGTGTAAA ATTCCTTGAC GAATACCAAT
         710        720        730        740        750
     CTAAAGTTAA AAGACAAATA TTTTCAGGCT ATCAATCTGA TATTGATACA
         760        770        780        790        800
     CATAATAGAA TTAAGGATGA ATTATGATTA AATTAAAATT TGGTGTTTTT
         810        820        830        840        850
     TTTACAGTTT TACTATCTTC AGCATATGCA CATGGAACAC CTCAAAATAT
         860        870        880        890        900
     TACTGATTTG TGTGCAGAAT ACCACAACAC ACAAATATAT ACGCTAAATG
         910        920        930        940        950
     ATAAGATATT TTCGTATACA GAATCTCTAG CTGGAAAAAG AGAGATGGCT
         960        970        980        990       1000
     ATCATTACTT TTAAGAATGG TGCAATTTTT CAAGTAGAAG TACCAAGTAG
        1010       1020       1030       1040       1050
     TCAACATATA GATTCACAAA AAAAAGCGAT TGAAAGGATG AAGGATACCC
        1060       1070       1080       1090       1100
     TGAGGATTGC ATATCTTACT GAAGCTAAAG TCGAAAAGTT ATGTGTATGG
        1110       1120       1130       1140       1150
     AATAATAAAA CGCCTCATGC GATTGCCGCA ATTAGTATGG CAAATTAA
```

FIG 6.

DNA SEQUENCES, RECOMBINANT DNA MOLECULES AND PROCESSES FOR PRODUCING THE A AND B SUBUNITS OF CHOLERA TOXIN AND PREPARATIONS CONTAINING SO-OBTAINED SUBUNIT OR SUBUNITS

The present invention relates to DNA sequences recombinant DNA molecules and processes for producing the A and B subunits of Cholera toxin and preparations containing so-obtained subunit or subunits.

It is known that the holotoxin produced by certain strains of *Vibrio cholerae* is composed of two protein subunits which are known as A and B subunits.

The A subunit (CTA) is responsible for epithelial cell penetration and the enzymatic effect leading to net loss of fluid into the gut lumen, whereas the B subunit (CTB) binds the holotoxin to monosialosylganglioside $G_{M1}$ receptor sites on the cell wall, possesses no toxic activity and is highly immunogenic.

Among the *Vibrio cholerae* strains producing the holotoxin are for instance the well known *Vibrio cholerae* biotype El Tor serotype INABA strains and, in Proc. Natl. Acad. Sci. USA 76, 2052-2056, 1979, T. HONDA and R. A. FINKELSTEIN described a *Vibrio cholerae* mutant which produces the B subunit but no detectable A subunit of the cholera toxin.

Existing cholera vaccines containing either lipopolysaccharides extracted from vibrios or dense killed vibrio suspensions can, after repeated injection, confer limited protection to heavily exposed contacts but they are not effective as an epidemic control measure. It has also been demonstrated in human volunteers that, after recovery from cholera, antibodies to the homologous organism and a high degree of resistance to it but not to heterologous strains are present.

Considering that cholera holotoxin is highly antigenic and that there is only one immunologic type, it has been suggested that an effective antitoxic immunity should protect against the various serotypes and biotypes of *V. cholera*.

With that view, the B subunit appears to be a desirable vaccine component to induce protective antibodies either by oral or parenteral administration and different authors have proposed cholera vaccines based on the B subunit toxin or, less preferably, toxoids (J. HOLMGREN et al. in Nature 269, 602-603, 1977; HONDA and R. A. FINKELSTEIN in op. cit. and J. HOLMGREN in Nature 292, 413-417, 1981).

Prior to this invention, it was also known that the holotoxin is specified by a chromosomal gene (ctx) and S. L. MOSELEY and S. FALKOW (J. Bact. 144, 444-446, 1980) have shown that DNA fragments representing the two cistrons of the related heat labile enterotoxin gene (elt) of *E. coli* can be used as probes in DNA/DNA hybridization experiments to detect specific ctx gene fragments of *V. cholerae* total DNA digested with various restriction endonucleases.

We have found and this is an object of the present invention that digestion of DNA of a toxigenic *Vibrio cholerae* strain producing the holotoxin (which strain is herein exemplified by a *Vibrio cholerae* El Tor INABA strain which has been deposited with the American Type Culture Collection, Rockville, Md, U.S.A. under accession number ATCC 39050) with ClaI endonuclease releases two distinct bands of DNA which hybridize respectively and exclusively to the eltB and eltA probes and therefore contain the related ctxB and ctxA cistrons.

According to the invention, the fragments containing either the ctxA or ctxB gene and obtained by ClaI endonuclease treatment as indicated hereinabove are then inserted either separately or sequentially into an appropriate vector which has been previously cleaved by ClaI endonuclease, to constitute cloning vehicles in nost microorganisms such as for instance an *E. coli* K12 strain or a non toxigenic *V. cholerae* strain. The finally obtained strains are then used for the production of either the A subunit or the B subunit or both A and B subunits of the cholera toxin or genetically modified derivatives thereof.

Figure 3:
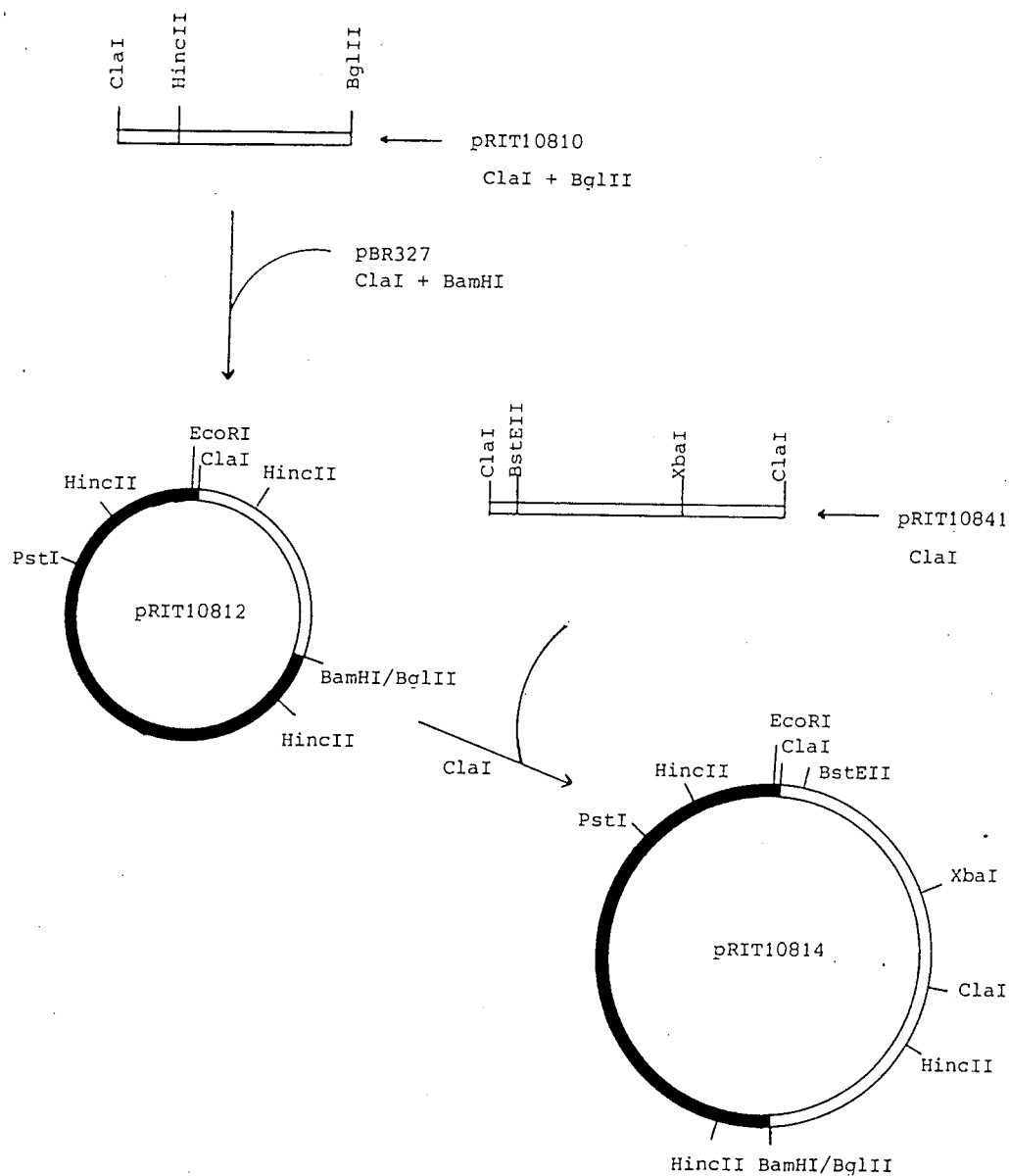

More particularly and as exemplified hereafter a
$1.0 \times 10^6$ a ClaI generated DNA fragment containing the major part of the ctxA gene has been cloned on plasmid pBR322, as shown in FIG. 1 which represents the restriction map of the $1.0 \times 10^6$ daltons insert on the so-obtained recombinant plasmid pRIT10841.

a $2.45 \times 10^6$ d ClaI generated DNA fragment containing the ctxB gene has been cloned on plasmid pBR322, as shown in FIG. 2 which represents the restriction map of the $2.45 \times 10^6$ daltons insert on the so-obtained recombinant plasmid pRIT10810. fragments containing both ctxA and ctxB genes have been cloned on plasmid pBR327 as a $0.75 \times 10^6$ daltons ClaI-BglII ctxB insert joined to the $1.0 \times 10^6$d ClaI ctxA insert, as shown in FIG. 3 which represents the restriction map of the inserts on the so-obtained recombinant plasmid pRIT10814.

Samples of an *E. coli* K12 strain have been transformed with the inclusion of the plasmids pRIT10841, pRIT10810 and pRIT10814, respectively and cultures of these transformed strains have been deposited with the American Type Culture Collection, Rockville, Md., U.S.A. under the respective accession number ATCC 39053, ATCC 39051 and ATCC 39052.

Furthermore a $5.1 \times 10^6$ d PstI DNA fragment has been cloned from ATCC 39050 onto the plasmid vector pBR322 to form the recombinant plasmid pRIT10824. This plasmid has the same number and disposition of restriction sites in and around the ctx coding sequences as the aforementioned pRIT10814.

It is obvious that the above process is not restricted to the exemplified ATCC 39050 strain and that when using as starting material a *V. cholerae* strain producing either the A subunit only or the B subunit only, bands of DNA containing either the ctxA cistron or the ctxB cistron will be obtained, respectively.

If proceeding with cloning of ClaI digested DNA of the classical *Vibrio cholerae* strain 569B (ATCC 25870) which contains two copies of the toxin gene, fragments of $1.25 \times 10^6$ d would be chosen as representing the ctxA sequences and fragments of either $0.88 \times 10^6$ d and/or $0.78 \times 10^6$ d would be chosen as representing the ctxB sequences.

Either each of the A and B subunits or both together are valuable for the preparation of cholera vaccines for which the A subunit is necessarily used in the form of a toxoid and the B subunit is less preferably used in the form of a toxoid.

According to another embodiment of the present invention, the cloned DNA fragments are employed to generate toxoid forms of the A or B subunits by genetic manipulation in vivo or in vitro. Examples of this well known to those skilled in the art are the creation of deletions or insertions of nucleotide base pairs at specific restriction sites or directed site specific mutagenesis to change particular amino acids. Furthermore it is also practicable to create hybrid toxin molecules by in vitro genetic manipulation, for example by recombining the related neat labile enterotoxin gene of *E. coli* with the present cloned cholera toxin gene at their homologous XbaI restriction sites in such a fashion as to replace the cholera toxin gene promoter region, the leader or signal peptide and the first nine amino acids of the mature A subunit protein by the corresponding LT sequences Expression of such a hybrid toxin consisting mainly of cholera toxin sequences would thus be regulated by an *E. Coli* promoter region presenting advantages for synthesis of the toxin in *E. coli* cells.

Pharmaceutical formulations containing either the B subunit or a toxoid and valuable as vaccines to be administered by oral and/or parenteral routes are prepared according to any technique known in the art for such preparation, i.e. for instance either by addition of an antacid such as sodium bicarbonate or by enteric coating or microencapsulation of the active ingredient; the toxoid is also easily obtained from the toxin e.g. by treatment with formaldehyde or, preferably, glutaraldehyde.

The A and B subunits of the present invention are also valuable for the characterization of environmental strains of *V. cholerae* by their possible use as radiolabelled probes in DNA/DNA hybridization experiments to detect ctxA and/or ctxB genes fragments in unknown *V. cholerae* strains upon digestion of their total DNA with restriction endonucleases or by colony hybridizations.

The invention is illustrated by the following examples.

EXAMPLE 1

Preparation of DNA of *V. cholerae* ATCC 39050

*V. cholerae* ATCC 39050 is allowed to grow in syncase medium (FINKELSTEIN et al. J. Immunol. 96, 440–449, (1966) to reach stationary phase. The cells are then recovered by centrifugation, washed and resuspended in a buffer containing 0.05 M tromethamine, 0.1M NaCl, 0.25M edetic acid (EDTA), pH 8.0. Cells are lysed by the addition of sodium dodecyl sulfate (SDS) to 1% (w/v) final concentration and the mixture extracted twice (with equal volumes of buffer saturated phenol. The DNA is precipitated with two volumes of cold ethanol, recovered by spooling onto a glass rod and dissolved in 1×SSC (1×SSC is standard saline citrate, i.e.: 0.15 M NaCl, 0.015M trisodium citrate, pH 7.0).

Tromethamine buffer (pH 8.0) is added to 0.05M final concentration and the preparation incubated with bovine pancreatic ribonuclease (10 μg/ml final concentration) for 1 hour at 37°. The mixture is extracted twice with equal volumes of buffer saturated phenol, the DNA precipitated with ethanol, dissolved in 1×SSC and dialyzed against 1×SSC.

A sample of 6 μg of the obtained DNA is digested with 45.6 units of ClaI endonuclease for 3 hours at 37° C. in a total volume of 40 μl.

The ClaI digested *Vibrio cholerae* DNA is divided into two equal samples and electrophoresed in separate slots of a 1% agarose gel (the electrophoresis buffer is that described by HAYWARD G. S. and SMITH M. G., J. Mol. Biol. 63, 383, (1972) and contains 0.5 μg/ml ethidium bromide).

Samples of DNA of phage lambda sequentially digested with HindIII and EcoRI restriction endonucleases are run in other slots of the same gel to serve as molecular weight markers using the values given by CORY, S. and ADAMS, J. Cell 11, 795 (1977).

After electrophoresis the gel is illuminated with short wave ultraviolet light to visualize the DNA fragments and photographed to preserve a record of the relative migration of the phage lambda DNA bands. DNA fragments in the gel are then transferred and bound to a nitrocellulose filter by the technique of SOUTHERN E. M., J. Mol. Biol. 98, 503 (1975).

The filter is cut in two lengthwise so as to obtain samples of *V. cholerae* DNA digested with ClaI on each half of the filter.

EXAMPLE 2

Preparation of eltA and eltB gene specific DNA probes pEWD299 plasmid DNA is prepared using CsCl density gradient centrifugation by the method described by KAHN M. et al., Methods in Enzymology, 68, 268, (1979) and the desired DNA fragments are separated and purified by digesting 50 to 100 μg of pEWD299 plasmid DNA with an excess of either the restriction endonucleases HincII (for eltA) or sequentially with restriction endonuclease HindIII and EcoRI (for eltB) followed by electrophoresis on 7.5% acrylamide gel. The construction and characterization of plasmid pEWD299 has been described by DALLAS W. and coll. in J. Bact. 139, 850 (1979).

That portion of the gel containing the desired fragment (the eltA gene fragment is a 1000 base pair DNA fragment and the eltB gene fragment is a 600 base pair DNA fragment) is excised with a scalpel, placed in a sac of dialysis membrane and the DNA eluted from the gel slice by electrophoresis. DNA eluted into the electrophoresis buffer within the sac is recovered and concentrated by ethanol precipitation. The DNA recovered is dissolved in 20 μl of 0.01 M-tromethamine buffer, pH 7.0.

The obtained eltA and eltB gene specific DNA fragments are those described by MOSELEY S. and FALKOW S., J. Bacteriol. 144, 444 (1980).

EXAMPLE 3

Labelling of DNA probe fragments by nick translation

Aliquots (0.5 μg) of the eltA and eltB DNA fragments purified as described in Example 2 are labelled in separate reaction mixtures with deoxycytidine 5'-triphosphate ($\alpha$-$^{32}$P) by the method known as nick translation (RIGBY P. et al., J. Mol. Biol. 113, 237 (1977)) using the kit (NEK-004) and reaction conditions supplied by New England Nuclear (Dreieich, Fed. Rep. Germany).

The specific activities of the DNA fragments so labelled are: $2.3\times10^7$ cpm per 0.5 μg DNA for the eltA DNA, and $3.14\times10^7$ cpm per 0.5 μg DNA for the eltB DNA. The labelled DNA is then denaturated before use by heating at 100° C. for 10 to 15 minutes.

EXAMPLE 4

Hybridization of filter bound DNA with the eltA probe

One half of the nitrocellulose filter containing bound, denaturated *V. cholerae* DNA fragments prepared as described in Example 1 is incubated for 3 hours at 37° in a prehybridization solution containing 5×SSC, 1 mM EDTA pH 8.0, 0.1% w/v sodium dodecyl sulfate (SDS), 1% v/v of the solution described by DENHARDT D., Biochem. Biophys. Res. Comm. 23, 641 (1966) prepared as a 100 fold concentrated solution and 25% v/v desionised formamide. The filter is then placed in a hybridization solution of the same composition but containing in addition 25 μg per ml heat denatured salmon sperm DNA and the radioactive, denatured eltA probe of Example 3 diluted to give a final specific activity of $9 \times 10^5$ cpm per ml. The filter is incubated in this solution for 36 hours at 37° and thereafter incubated twice for 25 minutes at 37° in solutions of the same compositions as used for hybridization but from which the radioactive probe DNA had been omitted. The filter is then rinsed twice for 25 minutes at room temperature in solutions of 0.2×SSC and air dried. The dried filter is exposed to X-ray film (Fuji Photo film Co. Ltd) for a time sufficient to darken areas of the film corresponding to those areas of the filter where radioactive probe DNA has hybridized to the bound denatured fragments of *V. cholerae* DNA.

Examination of X-ray films exposed to the filter incubated with the eltA probe shows that the eltA gene fragment hybridizes specifically and exclusively to a single band of ClaI digested total DNA of *Vibrio cholerae* ATCC 39050. This DNA fragment has an estimated molecular weight of $1.0 \times 10^6$ daltons by comparison to the relative migration of lambda DNA fragments. The *V. cholerae* DNA sequence showing homology in these hybridization conditions to the eltA probe represents all or part of the ctxA cistron which specifies the structural gene sequence for the subunit A of cholera toxin.

EXAMPLE 5

Hybridization of filter bound DNA with the eltB probe

An identical procedure is followed to hybridize radioactive eltB probe DNA with the other half filter containing bound denatured *V. cholerae* DNA except that a formamide concentration of 20% v/v is used and the eltB probe DNA is diluted to give a specific activity of $1.2 \times 10^6$ cpm per ml in the hybridization solution. The eltB probe hybridizes specifically and exclusively in the conditions described to a single band of ClaI digested *V. cholerae* ATCC 39050 DNA with an estimated molecular weight of $2.45 \times 10^6$ daltons.

The *V. cholerae* DNA sequence showing homology in these hybridization conditions to the eltB probe represents all or part of the ctxB cistron which specifies the structural gene sequence for the subunit B of cholera toxin.

EXAMPLE 6

Enrichment of DNA fragments containing either ctxA or ctxB gene sequences from total DNA of *V. cholerae*

A 63 μg aliquot of total DNA as obtained in Example 1 is digested for 3 hours at 37° with 500 units of ClaI endonuclease in a total reaction volume of 400 μ. The digested DNA is electrophoreses on a 1% (w/v) agarose gel. A sample of DNA of phage lambda digested with EcoRI and HindIII endonucleases and a sample of DNA of pEWD020 (W. DALLAS et al., J. Bacteriol. 139, 850 (1979)) digested with BamHI and EcoRI endonucleases are run in separate slots of the same gel to serve as molecular weight markers. The positions of *V. cholerae* DNA fragments from the ClaI endonuclease digest corresponding to molecular weights of 2.45×10 d and $1.0\times10^6$d are estimated by reference to the molecular weight markers and five 1 mm slices are cut crosswise from the gel at and above and below each of these two points. The DNA in each gel slice is recovered by electroelution in a closed sac of dialysis membrane. The fluid is removed from each sac, filtered through an 0.45μ Millipore filter to remove agarose fragments and the DNA recovered by precipitation with an equal volume of isopropanol. The precipitate is dissolved in 0.01 M tromethamine buffer pH 7.0 and reprecipitated with 2 volumes of ethanol. The DNA obtained from each gel slice is finally dissolved in 20 μl of 0.01 M tromethamine, 0.001M EDTA buffer, pH 7.0.

One μl samples of each DNA preparation are assayed for their content of ctxA or ctxB gene sequences by the dot hybridization method described by KAFATOS F. et al. (Nucl. Acids Res. 7, 1541 (1979)) and using the hybridization conditions and radioactive eltA and eltB probe DNAs described in Examples 2 to 5.

Two DNA preparations corresponding to $1.0\times10^6$d DNA are found to hybridize more strongly with the eltA probe than the other three.

Similarly two DNA preparations of DNA of $2.45\times10^6$ d hybridize more strongly with the eltB probe.

EXAMPLE 7

Cloning of DNA enriched for ctxB gene sequences

Aliquots (5 μg) of pBR322 plasmid DNA prepared by CsCl density gradient centrifugation are digested with 6.6 units of ClaI endonuclease for 2 hours at 37° in a reaction volume of 100 μl. To a 60 μl sample of this digest containing 3 μg of plasmid DNA are added 100 μl of glycine buffer (0.1M glycine, 1 mM $MgCl_2$ $6H_2O$, 0.1 mM $ZnSO_4$, 7 $H_2O$, pH 10.5) and 0.3 units of calf intestine alkaline phosphatase. The mixture is incubated 30 minutes at 37°, extracted twice with an equal volume of phenol, extracted three times with ether and the DNA precipitated with ethanol. The pBR322 DNA is dissolved in 30 μl of 0.01 M tromethamine-HCl, 0.001M EDTA buffer pH 7.0.

Aliquots (10 μl) of each of the two DNA fractions obtained in Example 6 and showing the strongest hybridization signal to the eltB probe are mixed with 0.4 μg of the ClaI digested, alkaline phosphatase treated pBR322 DNA and the mixture brought to a final volume of 30 μl with tromethamine buffer, extracted with an equal volume of phenol, extracted three times with ether, precipitated with ethanol and the DNA is dissolved in 20 μl of 0.01 M tromethamine-HCl, 0.001M EDTA buffer pH 7.0.

The mixture of *V. cholerae* DNA fragments and pBR322 DNA is ligated by incubation with T4-DNA ligase. To 10 μl of DNA mixture is added 10 μl of a T4-DNA ligase cocktail to give a solution containing 20 mM tromethamine HCl, pH 7.6, 10 mM $MgCl_2.6H_2O$, 10 mM dithiothreitol, 1.2 mM deoxyadenosine triphosphate, 50 μg per ml bovine serum albumin and 0.5 units of T4-DNA ligase (Boehringer Mannheim, Fed. Rep Germany).

The ligase containing mixture is incubated for 4 hours at 15° C. to obtain ligation of the *V. cholerae* DNA fragments to the ClaI digested pBR322 DNA and form recombinant molecules.

The total ligated DNA mixture (20 μl) is used to transform CaCl₂ treated competent cells of *E. coli* K12 strain MM294 (described by BACKMAN K. et al., Proc. Natl. Acad. Sci. U.S. 73, 4174 (1976)) prepared according to the procedure described by COHEN S. et al., Proc. Natl. Acad. Sci. U.S. 69, 2110 (1972). The transformed culture is spread on solid agar medium containing 200 μg per ml ampicillin to select for those cells which have taken up pBR322 plasmid DNA. Approximately 1000 ampicillin resistant colonies are recovered from the total transformed culture.

EXAMPLE 8

Screening of transformed colonies for ctxB gene sequences.

The ampicillin resistant transformed colonies obtained in Example 7 are screened for the presence of DNA sequences hybridizing to the eltB probe by the colony hybridization method described by GERGEN J. et al. Nucl. Acids Res. 7, 2115 (1979). Transformant colonies growing on the solid agar medium are transferred in fixed arrays to the surface of duplicate plates of ampicillin containing medium and the plates incubated at 37°. A square of sterile filter paper (Whatman 541) is placed on the surface of one plate of each pair and the bacterial growth stripped from the agar surface by removing the filter paper. By this procedure a replica is obtained on the filter paper of the colonies grown on the solid agar medium. The filter papers are dried for 15 minutes at 37° and processed as described by GERGEN J. et al. (loc. cit.) except that the ethanol wash is omitted.

The filter papers so treated are hybridized with the radioactive eltB probe DNA in exactly the same conditions and by the procedure described in Example 5 and exposed to X-ray film for varying periods of time.

Ten colonies are noted which are clearly darker than the rest and these are located and recovered from the duplicate agar plates. Of these 10 colonies showing a positive hybridization result, four are tetracycline sensitive, indicative of insertional inactivation of the tetracycline resistance gene on the pBR322 vector by a foreign DNA fragment.

Plasmid DNA is prepared from each of these four colonies by the procedure of BIRNBOIM H. and DOLY J. (Nucl. Acids Res. 7, 1513 (1979) and restriction analysis with ClaI endonuclease shows that in each preparation the pBR322 vector carries a DNA insert with a molecular weight of $2.45\times10^6$d. One so-isolated colony was characterized as being MM294 (pRIT10810) of which a culture has been deposited with the American Type Culture Collection under accession number ATCC 39051.

EXAMPLE 9

Characterization of ATCC 39051 strain

Plasmid. DNA was prepared from ATCC 39051 strain by CsCl-ethidium bromide density gradient centrifugation and subjected to further restriction endonuclease analysis. The $2.45\times10^6$ daltons ClaI DNA insert is characterized in having the restriction sites and orientation vis-a-vis the pBR322 vector DNA as shown in FIG. 1.

The strain was further characterized in producing a protein reacting with antibodies raised against pure cholera toxin in an enzyme linked immunosorbent assay described by SVENNERHOLM A. and HOLMGREN J. (Curr. Microbiol. 1, 19, 1978) and based on the binding of the B subunit protein of cholera toxin to GMl ganglioside receptors.

Extracts of broth grown cells of ATCC 39051 strain prepared by passage through a French pressure cell and clarified by centrifugation at $30{,}000\times g$ for 30 minutes at 4° C. were found to be strongly positive for B subunit protein by this ELISA assay.

To further characterize the cloned insert, pRIT10810 DNA was digested sequentially with ClaI and HincII endonucleases and the $0.2\times10^6$ fragment was purified by electrophoresis on an acrylamide gel and electroelution of the gel slice containing the fragment. 0.5 μg of this purified fragment was labelled with $^{32}P$ by nick translation as described in Example 3 to a specific activity of $1.96\times10^8$ cpm per 0.5 μg for use as a probe. Total DNA of ATCC 39050 strain was digested with various endonucleases and samples electrophoresed on agarose gels, denatured and transferred to nitrocellulose filters. These filters were incubated with the radioactive, denatured ClaIHincII probe DNA in stringent conditions of DNA/DNA hybridization, omitting formamide from the hybridization, omitting formamide from the hybridization solutions and performing the incubation at 65° for 18 hours.

Examination of X-ray films exposed to the hybridized nitrocellulose filters showed that exactly the same bands of Vibrio DNA were revealed with the Vibrio ClaI-HincII probe as had been detected in Example 5 with the eltB probe in less stringent conditions. This results shows that the cloned DNA is of *Vibrio cholerae* origin.

EXAMPLE 10

Cloning of *V. cholerae* DNA enriched for ctxA gene sequences

Ten μg of each of the two ClaI digested DNA fractions (showing the strongest hybridization signal to the eltA probe), described in Example 7, are mixed with 0.4 μg of ClaI digested and alkaline phosphatase treated pBR322 DNA.

The DNA mixture is extracted with phenol, alcohol precipitated, dissolved and ligated with T4-DNA ligase exactly as described in Example 7 and used to transform $CaCl_2$ treated cells of strain *E. coli* K12, MM294. A total of about 4000 colonies are recovered by inoculating the transformed culture on ampicillin containing agar medium at 37°.

The ampicillin resistant colonies described above were screened for the presence of DNA sequences hybridizing to the eltA probe using the procedures and conditions described in Example 8. Two colonies were detected which gave a positive response with the eltA probe and which were tetracycline sensitive. Plasmid DNA was prepared from these two clones by the method of BIRNBOIM and DOLY (loc. cit.) and digestion with ClaI endonuclease released, in addition to the pBR322 vector fragment, a DNA fragment of $1.0\times10^6$ d. The two colonies were characterized as being MM294 (pRIT10841) and MM294 (pRIT10851). A culture of MM294 (pRIT10841) has been deposited with the American Type Culture Collection under accession number ATCC 39053.

EXAMPLE 11

Characterization of ATCC 39053 strain

Plasmid DNA was prepared from ATCC 39053 strain by CsCl-ethidium bromide gradient centrifugation and subjected to further restriction endonuclease analysis. The $1.0 \times 10^6$ daltons DNA insert is characterized in having the placement of the BstEII and XbaI restriction sites and orientation vis-a-vis the pBR322 vector DNA as is shown in FIG. 2. The ClaI insert DNA is further characterized in having no sites for EcoRI, BamHI, HindIII, PstI, SacI, PvuI, XhoI, AvaI, BglII, HpaI, SmaI, HincII, PvuII or SalI endonucleases.

Purified DNA of pRIT10841 was digested with ClaI endonuclease and the $1.0 \times 10^6$ daltons fragment purified by agarose gel electrophoresis and electroelution. 0.5 µg of this DNA was labelled with $^{32}p$ by nick translation as described in Example 3 and used as a probe.

Total DNA of ATCC 39050 strain was digested with various restriction endonucleases and samples electrophoresed on agarose gels, denatured in situ and transferred to nitrocellulose filters. Incubation in stringent conditions of hybridization of the denatured ClaI probe DNA fragment to Vibrio DNA fixed to the filters showed that the probe detected exactly the same bands of Vibrio DNA as had been detected by the eltA probe in relaxed hybridization conditions.

This result shows that the cloned DNA is of Vibrio origin.

EXAMPLE 12

Construction of pRIT10812

A 25 µg aliquot of plasmid DNA of pRIT10810 prepared as described in Example 9 is digested sequentially with 55 units of ClaI endonuclease for 3 hours at 37° and 24 units of BglII endonuclease for 2 hours at 37°. The digested DNA is electrophoresed on a 1% agarose gel and the $0.75 \times 10^6$ daltons ClaI-BglII DNA fragment containing the ctxB gene sequences is cut from the gel and the DNA recovered by electroelution.

Plasmid DNA (2.5 g) of pBR327 (SOBERON X. et al., Gene 9, 287, 1980) is sequentially digested with 11 units of ClaI endonuclease for 2.5 hours at 37° C. and with 8 units of BamHI endonuclease for 2 hours at 37°. The digested DNA is extracted twice with phenol, 3 times with ether, ethanol precipitated and dissolved in 0.01 M tromethamine buffer pH 7.0. A 0.4 µg aliquot of the purified ClaI-BglII ctxB DNA fragment is ligated with 0.2 µg of ClaI and BaMHI digested DNA of pBR327 in the ligation conditions described above.

The ligated mixture of DNA is used to transform competent CaCl₂ treated cells of E. coli K12 strain MM294. Transformants are selected on solid agar medium containing ampicillin (200 µg/ml).

One of the so-isolated colonies was shown to contain a plasmid, pRIT10812, consisting of the major pBR327 ClaI-BamHI fragment with an insert of the ClaIBglII fragment purified from pRIT10810. The plasmid was characterized in having the restriction map shown in FIG. 3.

EXAMPLE 13

Combination of the ctxA and ctxB fragment—Construction of pRIT10814

A 51 µg aliquot of purified plasmid DNA of pRIT10841 prepared as described in Example 11 is digested with 27 units of ClaI endonuclease for 18 hours at 37°. The mixture is electrophoresed on a 1% agarose gel and a gel slice containing the $1.0 \times 10^6$ daltons ClaI DNA fragment excised.

The DNA is recovered from the gel slice by electroelution and ethanol precipitation.

A 2.86 µg aliquot of purified DNA of pRIT10812 prepared as described in Example 12 is digested with 11 units of ClaI endonuclease for 2 hours at 37° and treated with 0.25 units of calf intestine alkaline phosphatase as described in Example 7. The treated DNA is phenol extracted and ethanol precipitated. A 0.4 µg aliquot of this DNA is ligated with 0.5 µg of the purified ClaI DNA fragment isolated from pRIT 10841 in the ligation conditions described in Example 7 above. Half the ligated DNA mixture is used to transform competent CaCl₂ treated cells of E. coli K12 strain MM 294 with selection being made on solid agar medium with ampicilin (200 µg/ml). Plasmid DNA is prepared by the method of BIRNBOIM and DOLY (loc. cit.) from 12 colonies and restricted sequentially with PstI and XbaI endonucleases. One so-obtained plasmid gave a restriction fragment pattern indicative of insertion of the $1.0 \times 10^6$ daltons ClaI fragment on pRIT10812 in the desired orientation and was further characterized.

Plasmid DNA was prepared from the clone by CsClethidium bromide centrifugation.

The plasmid DNA of clone MM294 (pRIT10814) was shown by restriction endonuclease analysis to have the structure shown in FIG. 3. A culture of MM294 (pRIT10814) has been deposited with the American Type Culture Collection under the accession number ATCC 39052.

The above combination steps are schematized in FIG. 3.

The orientation of the $1.0 \times 10^6$ daltons ClaI DNA fragment from pRIT10841 on the recombinant plasmid pRIT10814 is deduced to be such as to juxtapose the ctxA sequence with the ctxB sequence at the ClaI site, i.e. to reform the complete cistrons specifying the structural gene for cholera toxin.

EXAMPLE 14

In vivo activity of ATCC 39052 strain

One ml samples of extracts of broth grown cells of ATCC 39052 strain prepared as described in Example 9 and containing 10 to 13 mg/ml total protein were injected into ligated intestinal loops of ten adult rabbits. The loops were examined 18 hours later and the fluid accumulation measured in each loop.

Considering that a ratio $\leqq 0.5$ means negative response and $\geqq 0.5$ means positive response, it appears from Table I that the extracts from ATCC 39052 strain gave a positive response in nine of ten animals.

In contrast, extracts of strain MM294 (pBR322) gave no measurable fluid accumulation in five animals tested. Injection of 100 ng purified cholera toxin per loop produced a positive response in eight of eight rabbits as did 10 ng purified toxin in three of eight rabbits. Extracts of ATCC 39051 strain (pRIT10810) and ATCC 39053 strain (pRIT10841) were also negative in tests on four and five rabbits respectively. This result shows that extracts of ATCC 39052 strain (pRIT10814) contain a substance capable of provoking an accumulation of fluid in the rabbit intestine as does cholera toxin. The ctxA and ctxB cistrons on pRIT10814 must therefore have been correctly religated at their common ClaI site so as to restore a functional structural gene specifying the synthesis of cholera holotoxin.

The results are given in Table I.

TABLE I

Adult rabbit intestinal loop test.

| Extract | No of rabbits tested | No giving positive response | Average ratio: fluid volume per cm intestinal loop |
|---|---|---|---|
| Strain MM294 (pBR322) | 5 | 0 | <0.1 |
| ATCC 39052 | 10 | 9 | 1.40 |
| ATCC 39051 | 4 | 0 | <0.1 |
| ATCC 39053 | 5 | 0 | <0.1 |
| Cholera toxin | | | |
| 100 ng/ml | 8 | 8 | 1.62 |
| 10 ng/ml | 8 | 3 | 0.66 |

EXAMPLE 15

Cloning of a PstI DNA fragment containing both ctxA and ctxB cistrons from V. cholerae ATCC 39050

To verify the completeness of the cloned ClaI DNA fragments encoding the ctxA and ctxB cistrons a DNA fragment encompassing both cistrons was directly cloned from strain ATCC 39050. Analysis of total ATCC 39050 DNA digested with PstI endonuclease with the eltA and eltB probes using the methods and procedures described above in Examples 1 to 5 showed that both the ctxA and ctxB cistrons were present on a DNA fragment or fragments with a calculated molecular weight of $5.3 \times 10^6$d.

This fragment was enriched from a digest of 50 μg ATCC 39050 DNA with 100 units of PstI endonuclease by the methods and procedures described in Example 6 and an aliquot of 6 μl of the fraction showing the strongest hybridization response with the ClaI-HindII ctxB probe of V. cholerae DNA described in Example 9 was ligated to 0.4 μg of pBR322 plasmid DNA previously digested with PstI. This ligated DNA mixture was transformed into E. coli K12 strain MM294 with transformant colonies being selected on solid agar medium supplemented with 15 μg/ml tetracycline.

These colonies (about 14000 total) were transferred to Whatman 541 filter papers, the filters processed as described in Example 8 and hybridized with the radioactive ctxA fragment probe described in Example 11.

Figure 4:
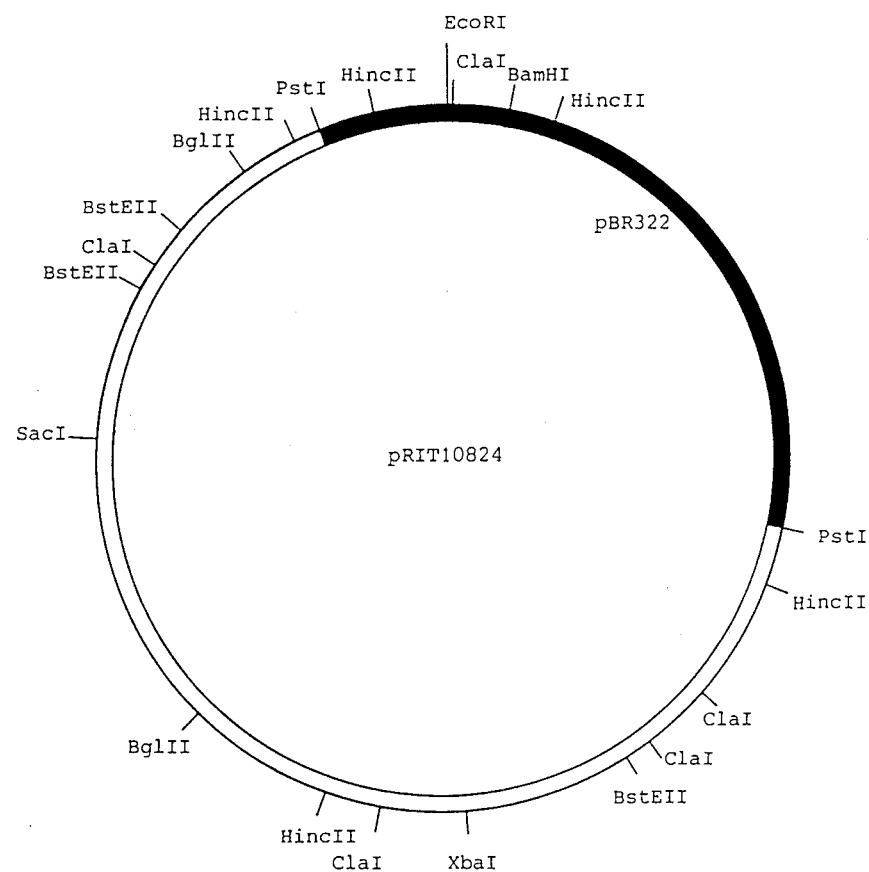

Eleven colonies were detected which showed a positive hybridization response to the ctxA probe and which were tetracycline resistant and ampicillin sensitive indicative of insertion of a foreign DNA fragment at the PstI site of the pBR322 vector. Plasmid DNA was prepared from one of these clones, strain MM294-(pRIT10824) and subjected to restriction enzyme analysis. The pRIT10824 plasmid contains a $5.1 \times 10^6$d insert at the PstI site of the vector and digestion with ClaI endonuclease releases 5 fragments of which one corresponds in size to the $1.0 \times 10^6$ d ctxB fragment previously cloned in pRIT10810 and one to the $2.45 \times 10^6$ d ctxA fragment previously cloned in pRIT10841. In addition these $1.0 \times 10^6$ d and $2.45 \times 10^6$ d ClaI fragments from pRIT10824 possessed the same number and location of restriction sites as did the separately cloned fragments in pRIT10810 and pRIT10841. Furthermore comparison of restriction enzyme digests between pRIT10824 and pRIT10814 described in Example 13 showed no difference in the number of restriction fragments for enzymes or combinations of enzymes cutting in or around the ctx cistrons. A restriction map of pRIT10824 is shown in FIG. 4.

EXAMPLE 16

DNA sequences of the ctxA and ctx B cistrons

The nucleotide sequence of the DNA corresponding to the ctxA and ctxB cistrons was determined by the chemical modification method of MAXAM and GILBERT using the procedures described in Methods in Enzymology, 65, 499–560, 1980. Purified restriction fragments were labelled with $^{32}$p at their 5' end either by exchange kination or by direct kination of dephosphorylated ends. Alternatively, 3' ends were labelled using terminal transferase and α-$^{32}$p-cordycepin (C.P. TU and S.N. COHEN, Gene, 10, 177–183, 1980). Fragments labelled at only one end were obtained by cleavage with a further restriction endonuclease and purification on polyacrylamide gel. The dimethylsulfate, hydrazine and sodium hydroxide reactions were used respectively for cleavage at guanine, pyrimidine and adenine. After piperidine cleavage the products were separated on thin 8% or 20% polyacrylamide gels (SANGER & COULSON, FEBS lett. 87, 107, 1978). The sequence was then read from the autoradiogram of the gel.

Figure 5:
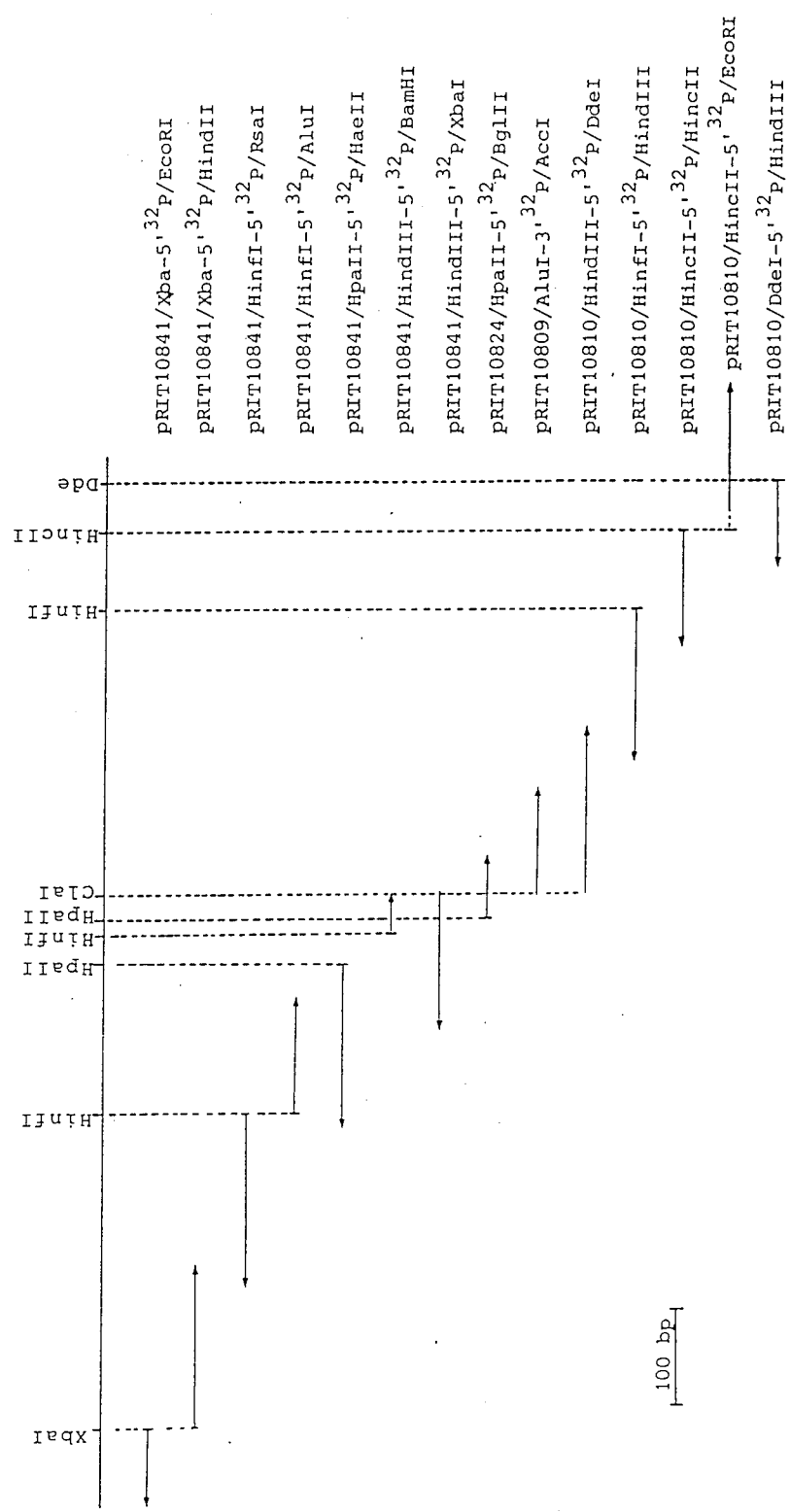

To ensure the greatest degree of precision in the sequence determination, overlapping DNA sequences were read from different labelled ends and both strands of the DNA sequenced wherever possible. The recombinant plasmids, the restriction sites chosen for labelling and the extent of sequence read in each determination are shown in FIG. 5.

The DNA sequence derived by these methods is shown in FIG. 6 and comprises 1148 nucleotides of which nucleotides 1 to 777 inclusive form the coding sequence for the A subunit and nucleotides 774 to 1148 inclusive form the coding sequence for the B subunit. It is important that in the present sequence there exist extensive regions which correspond to known amino acid sequences for the A subunit and B subunit proteins of E. coli heat labile enterotoxin (see SPICER E. and coll.: Proc. Natl. Acad. Sci. US 78, 50, 1981) always excepting errors and omission in such protein sequence determinations. It is also to be realised that variations in codons and amino acids may exist between different strains of Vibrio cholerae for both the A and B subunits and that the present invention is not limited to the sequence described above but includes all functional equivalents of the above described sequence. This is exemplified by comparison of the B subunit protein sequence for the present El Tor Vibrio strain and the known amino acid sequence determined by LAI (J. Biol. Chem. 252, 7249, 1977) for the B protein of the classical Vibrio strain 569B (ATCC 25870) where five amino acid differences exist, notably at positions 18, 22, 47, 54 and 70, in the mature amino acid sequence.

It is also to be noted that the coding sequence of the A subunit protein runs through the ClaI site marking the end of the ctxA gene fragment extending into and terminating at nucleotide 777 within the so called ctxB gene fragment.

EXAMPLE 17

Vaccine preparation

E. coli ATCC 39051 strain is allowed to grow in syncase medium (loc. cit.) to reach stationary phase. The culture is then centrifuged and filtered and the resulting filtrate is concentrated, dialyzed and adsorbed with aluminium hydroxide. After washing, the solution of subunit B of cholera toxin is eluted with 0.1 M sodium citrate, buffered at pH 7.2 with phosphate buffer, distributed into 2 ml vials containing 200 antitoxin units per ml and freeze-dried.

Freshly rehydrated vials are used for oral administration, the vaccination schedule comprising a booster administration 30 days after the first one, each administration being preceded by oral administration of 2 g of sodium bicarbonate in 60 ml of water.

We claim:

1. A recombinant DNA molecule comprising at least a portion coding for subunits A and B of cholera toxin, or a fragment or derivative of said portion wherein the fragment or derivative codes for a polypeptide having an activity which (a) can induce an immune response to subunit A; (b) can induce an immune response to subunit A and cause epithelial cell penetration and the enzymatic effect leading to net loss of fluid into the gut lumen; (c) can bind to the membrane receptor for the B subunit of cholera toxin; (d) can induce an immune response to subunit B; (e) can induce an immune response to subunit B and bind to said membrane receptor; or (f) has a combination of said activities.

2. A DNA sequence of the formula:

toxin or for a polypeptide having an activity which (a) can induce an immune response to subunit A; (b) can induce an immune response to subunit A and cause epithelial cell penetration and the enzymatic effect leading to net loss of fluid into the gut lumen; (c) can bind to the membrane receptor for the B subunit of cholera toxin; (d) can induce an immune response to subunit B; (e) can induce an immune response to subunit B and bind to said membrane receptor; or (f) has a combination of said activities.

3. A recombinant DNA molecule according to claim 1 wherein the portion coding for said subunits A and B of cholera toxin or the fragment or derivative of said portion is operatively linked to an expression control sequence.

4. The recombinant DNA molecule pRIT18014.

5. A host microorganism transformed with at least one recombinant DNA molecule according to claim 3.

6. The E. coli ATCC 39052 strain.

7. A recombinant DNA molecule according to claim 1 comprising at least a portion coding for subunit A of cholera toxin, or a fragment or derivative of said portion wherein the fragment or derivative codes for a polypeptide which can induce an immune response to subunit A of cholera toxin or which can induce an im-

```
5'-
        10           20           30           40           50
   ATGGTAAAGA   TAATATTTGT   GTTTTTTATT   TTCTTATCAT   CATTTTCATA
        60           70           80           90          100
   TGCAAATGAT   GATAAGTTAT   ATCGGGCAGA   TTCTAGACCT   CCTGATGAAA
       110          120          130          140          150
   TAAAGCAGTC   AGGTGGTCTT   ATGCCAAGAG   GACAGAGTGA   GTACTTTGAC
       160          170          180          190          200
   CGAGGTACTC   AAATGAATAT   CAACCTTTAT   GATCATGCAA   GAGGAACTCA
       210          220          230          240          250
   GACGGGATTT   GTTAGGCACG   ATGATGGATA   TGTTTCCACC   TCAATTAGTT
       260          270          280          290          300
   TGAGAAGTGC   CCACTTAGTG   GGTCAAACTA   TATTGTCTGG   TCATTCTACT
       310          320          330          340          350
   TATTATATAT   ATGTTATAGC   CACTGCACCC   AACATGTTTA   ACGTTAATGA
       360          370          380          390          400
   TGTATTAGGG   GCATACAGTC   CTCATCCAGA   TGAACAAGAA   GTTTCTGCTT
       410          420          430          440          450
   TAGGTGGGAT   TCCATACTCC   CAAATATATG   GATGGTATCG   AGTTCATTTT
       460          470          480          490          500
   GGGGTGCTTG   ATGAACAATT   ACATCGTAAT   AGGGGCTACA   GAGATAGATA
       510          520          530          540          550
   TTACAGTAAC   TTAGATATTG   CTCCAGCAGC   AGATGGTTAT   GGATTGGCAG
       560          570          580          590          600
   GTTTCCCTCC   GGAGCATAGA   GCTTGGAGGG   AAGAGCCGTG   GATTCATCAT
       610          620          630          640          650
   GCACCGCCGG · GTTGTGGGAA   TGCTCCAAGA   TCATCGATGA   GTAATACTTG
       660          670          680          690          700
   CGATGAAAAA   ACCCAAAGTC   TAGGTGTAAA   ATTCCTTGAC   GAATACCAAT
       710          720          730          740          750
   CTAAAGTTAA   AAGACAAATA   TTTTCAGGCT   ATCAATCTGA   TATTGATACA
       760          770          780          790          800
   CATAATAGAA   TTAAGGATGA   ATTATGATTA   AATTAAAATT   TGGTGTTTTT
       810          820          830          840
   TTTACAGTTT   TACTATCTTC   AGCATATGCA   CATGGAACAC   CTCAAAATAT
       860          870          880          890          900
   TACTGATTTG   TGTGCAGAAT   ACCACAACAC   ACAAATATAT   ACGCTAAATG
       910          920          930          940          950
   ATAAGATATT   TTCGTATACA   GAATCTCTAG   CTGGAAAAAG   AGAGATGGCT
       960          970          980          990         1000
   ATCATTACTT   TTAAGAATGG   TGCAATTTTT   CAAGTAGAAG   TACCAAGTAG
      1010         1020         1030         1040         1050
   TCAACATATA   GATTCACAAA   AAAAAGCGAT   TGAAAGGATG   AAGGATACCC
      1060         1070         1080         1090         1100
   TGAGGATTGC   ATATCTTACT   GAAGCTAAAG   TCGAAAAGTT   ATGTGTATGG
      1110         1120         1130         1140         1150
   AATAATAAAA   CGCCTCATGC   GATTGCCGCA   ATTAGTATGG   CAAATTAA
                                                              -3'
``` and fragments and derivatives thereof, said fragments and derivatives coding for subunits A and B of cholera mune response to subunit A and cause epithelial cell penetration and the enzymatic effect leading to net loss of fluid into the gut lumen.

8. A fragment of the DNA sequence according to claim 2 of the formula:

13. A recombinant DNA molecule according to claim 1 comprising at least a portion coding for subunit B of cholera toxin, or a fragment or derivative of said portion wherein the fragment or derivative codes for a polypeptide which can induce an immune response to

| 5'- | | | | |
|---|---|---|---|---|
| 10 | 20 | 30 | 40 | 50 |
| ATGGTAAAGA | TAATATTTGT | GTTTTTATT | TTCTTATCAT | CATTTTCATA |
| 60 | 70 | 80 | 90 | 100 |
| TGCAAATGAT | GATAAGTTAT | ATCGGGCAGA | TTCTAGACCT | CCTGATGAAA |
| 110 | 120 | 130 | 140 | 150 |
| TAAAGCAGTC | AGGTGGTCTT | ATGCCAAGAG | GACAGAGTGA | GTACTTTGAC |
| 160 | 170 | 180 | 190 | 200 |
| CGAGGTACTC | AAATGAATAT | CAACCTTTAT | GATCATGCAA | GAGGAACTCA |
| 210 | 220 | 230 | 240 | 250 |
| GACGGGATTT | GTTAGGCACG | ATGATGGATA | TGTTTCCACC | TCAATTAGTT |
| 260 | 270 | 280 | 290 | 300 |
| TGAGAAGTGC | CCACTTAGTG | GGTCAAACTA | TATTGTCTGG | TCATTCTACT |
| 310 | 320 | 330 | 340 | 350 |
| TATTATATAT | ATGTTATAGC | CACTGCACCC | AACATGTTTA | ACGTTAATGA |
| 360 | 370 | 380 | 390 | 400 |
| TGTATTAGGG | GCATACAGTC | CTCATCCAGA | TGAACAAGAA | GTTTCTGCTT |
| 410 | 420 | 430 | 440 | 450 |
| TAGGTGGGAT | TCCATACTCC | CAAATATATG | GATGGTATCG | AGTTCATTTT |
| 460 | 470 | 480 | 490 | 500 |
| GGGGTGCTTG | ATGAACAATT | ACATCGTAAT | AGGGGCTACA | GAGATAGATA |
| 510 | 520 | 530 | 540 | 550 |
| TTACAGTAAC | TTAGATATTG | CTCCAGCAGC | AGATGGTTAT | GGATTGGCAG |
| 560 | 570 | 580 | 590 | 600 |
| GTTTCCCTCC | GGAGCATAGA | GCTTGGAGGG | AAGAGCCGTG | GATTCATCAT |
| 610 | 620 | 630 | 640 | 650 |
| GCACCGCCGG | GTTGTGGGAA | TGCTCCAAGA | TCATCGATCA | GTAATACTTG |
| 660 | 670 | 680 | 690 | 700 |
| CGATGAAAAA | ACCCAAAGTC | TAGGTGTAAA | ATTCCTTGAC | GAATACCAAT |
| 710 | 720 | 730 | 740 | 750 |
| CTAAAGTTAA | AAGACAAATA | TTTTCAGGCT | ATCAATCTGA | TATTGATACA |
| 760 | 770 | 780 | 790 | 800 |
| CATAATAGAA | TTAAGGATGA | ATTATGA | | |
| | | | | -3' | and fragments and derivatives thereof, said fragments and derivatives coding for subunit A of cholera toxin or for a polypeptide which can induce an immune response to subunit A of cholera toxin or which can induce an immune response to subunit A and cause epithelial cell penetration and the enzymatic effect leading to net loss of fluid into the gut lumen.

9. A recombinant DNA molecule according to claim 7 wherein the portion coding for said subunit A of cholera toxin or the fragment or derivative of said portion is operatively linked to an expression control sequence.

10. The recombinant DNA molecule pRIT10841.

11. A host microorganism transformed with at least one recombinant DNA molecule according to claim 9.

12. The E. coli ATCC 39053 strain.

subunit B of cholera toxin or which can bind to the membrane receptor for subunit B of cholera toxin or which can both induce such immune response and bind to said membrane receptor.

14. A fragment of the DNA sequence according to claim 2 of the formula:

| 5'- | | | | |
|---|---|---|---|---|
| | | 780 | 790 | 800 |
| | | ATGATTA | AATTAAAATT | TGGTGTTTTT |
| 810 | 820 | 830 | 840 | 840 |
| TTTACAGTTT | TACTATCTTC | AGCATATGCA | CATGGAACAC | CTCAAAATAT |
| 860 | 870 | 880 | 890 | 900 |
| TACTGATTTG | TGTGCAGAAT | ACCACAACAC | ACAAATATAT | ACGCTAAATG |
| 910 | 920 | 930 | 940 | 950 |
| ATAAGATATT | TTCGTATACA | GAATCTCTAG | CTGGAAAAAG | AGAGATGGCT |
| 960 | 970 | 980 | 990 | 1000 |
| ATCATTACTT | TTAAGAATGG | TGCAATTTTT | CAAGTAGAAG | TACCAAGTAG |
| 1010 | 1020 | 1030 | 1040 | 1050 |
| TCAACATATA | GATTCACAAA | AAAAAGCGAT | TGAAAGGATG | AAGGATACCC |
| 1060 | 1070 | 1080 | 1090 | 1100 |
| TGAGGATTGC | ATATCTTACT | GAAGCTAAAG | TGAAAAGTT | ATGTGTATGG |
| 1110 | 1120 | 1130 | 1140 | 1150 |
| AATAATAAAA | CGCCTCATGC | GATTGCCGCA | ATTAGTATGG | CAAATTAA |
| | | | | -3' | and fragments and derivatives thereof, said fragments and derivatives coding for subunit B of cholera toxin or for a polypeptide which can induce an immune response to subunit B of cholera toxin or which can bind to the membrane receptor for subunit B of cholera toxin or which can both induce such immune response and bind to said membrane receptor.

15. A recombinant DNA molecule according to claim 13 wherein the portion coding for said subunit B of cholera toxin or the fragment or derivative of said portion is operatively linked to an expression control sequence.

16. The recombinant DNA molecule pRIT10810.

17. A host microorganism transformed with at least one recombinant DNA molecule according to claim 15.

18. The process for preparing a recombinant DNA molecule selected from the group consisting of a recombinant DNA molecule comprising at least a portion coding for subunit A of cholera toxin or a fragment or derivative of said portion wherein the fragment or derivative codes for a polypeptide which can induce an immune response to subunit A of cholera toxin or which can induce an immune response to subunit A and cause epithelial cell penetration and the enzymatic effect leading to net loss of fluid into the gut lumen and the recombinant DNA molecule pRIT10841, comprising digesting DNA of a *V. cholerae* strain producing subunit A of the cholera toxin with Cla I endonuclease; isolating a fragment having specific hybridization to an eltA probe; mixing said fragment with a vector having a Cla I endonuclease restriction site and previously Cla I digested; and inserting the fragment into said vector.

19. A process for producing subunit A of cholera toxin comprising providing a recombinant DNA molecule, said recombinant DNA molecule comprising the sequence coding for subunit A of cholera toxin; inserting said recombinant DNA molecule at a Cla I endonuclease restriction site of an appropriate vector to produce a hybrid vector; transforming an appropriate host with said hybrid vector; culturing the transformed host; allowing the transformed host to synthesize subunit A of cholera toxin; and collecting said subunit A of cholera toxin.

20. A process according to claim 19 wherein the appropriate vector is plasmid pBR322.

21. The process for preparing a recombinant DNA molecule selected from the group consisting of a recombinant DNA molecule comprising at least a portion coding for subunit B of cholera toxin, or a fragment or derivative of said portion wherein the fragment or derivative codes for a polypeptide which can induce an immune response to subunit B of cholera toxin or which can bind to the membrane receptor for subunit B of cholera toxin or which can both induce such immune response and bind to said membrane receptor and the recombinant DNA moledule pRIT10810, comprising digesting DNA of a *V. cholerae* strain producing subunit B of the cholera toxin with Cla I endonuclease; isolating a fragment showing specific hybridization to an eltB probe; mixing said fragment with a vector having a Cla I endonuclease restriction site and previously Cla I digested; and inserting the fragment into said vector.

22. A process for producing subunit B of cholera toxin comprising providing a recombinant DNA molecule, said recombinant DNA molecule comprising the sequence coding for subunit B of cholera toxin; inserting said recombinant DNA molecule at a Cla I endonuclease restriction site of an appropriate vector to produce a hybrid vector; transforming an appropriate host with said hybrid vector; culturing the transformed host; allowing the transformed host to synthesize subunit B of cholera toxin; and collecting said subunit B of cholera toxin.

23. The process for preparing a recombinant DNA molecule selected from the group consisting of a recombinant DNA molecule comprising at least a portion coding for subunits A and B of cholera toxin, or a fragment or derivative of said portion wherein the fragment or derivative codes for a polypeptide having an activity which (a) can induce an immune response to subunit A; (b) can induce an immune response to subunit A and cause epithelial cell penetration and the enzymatic effect leading to net loss of fluid into the gut lumen; (c) can bind to the membrane receptor for the B subunit of cholera toxin; (d) can induce an immune response to subunit B; (e) can induce an immune response to subunit B and bind to said membrane receptor; or (f) has a combination of said activities and the recombinant DNA molecule pRIT10814, comprising digesting a DNA sequence encoding subunit B of the cholera toxin sequentially with Cla I and an endonuclease not cutting the sequence coding for B subunit; isolating the resulting fragment; inserting said fragment into an adequate vector which has been sequentially digested with Cla I endonuclease and a second appropriate endonuclease to yield a recombinant DNA molecule which recombinant DNA molecule is then either (g) digested with Cla I endonuclease or (h) digested sequentially with Cla I endonuclease and a second endonulcease and wherein the DNA fragment resulting from (g) or (h) is combined with a DNA fragment obtained by digesting DNA from a *V. cholerae* strain producing subunit A of the cholera toxin with either (i) Cla I endonuclease or (j) Cla I endonuclease and sequentially a second endonuclease.

24. A process for producing subunits A and B of cholera toxin comprising providing a recombinant DNA molecule, said recombinant DNA molecule comprising the sequence coding for subunit A of cholera toxin and the sequence coding for subunit B of cholera toxin; inserting said recombinant DNA coding for subunit A and subunit B of cholera toxin and the expression control sequence for said recombinant DNA coding for subunit A of cholera toxin at a Cla I endonuclease restriction site of an appropriate vector to produce a hybrid vector; transforming an appropriate host with said hybrid vector; culturing the transformed host; allowing the transformed host to synthesize subunits A and B of cholera toxin; and collecting said subunits A and B of cholera toxin.

25. A process according to claim 24 wherein the hybrid vector is plasmid pRIT10812.

26. The *E. coli* ATCC 39051 strain.

* * * * *